(12) United States Patent
Chang

(10) Patent No.: US 9,155,561 B2
(45) Date of Patent: Oct. 13, 2015

(54) MINI-RAIL EXTERNAL FIXATOR

(71) Applicant: Stryker Trauma SA, Selzach (CH)

(72) Inventor: Eric Chang, East Brunswick, NJ (US)

(73) Assignee: Stryker Trauma SA (CH)

( * ) Notice: Subject to any disclaimer, the term of this patent is extended or adjusted under 35 U.S.C. 154(b) by 108 days.

(21) Appl. No.: 13/786,748

(22) Filed: Mar. 6, 2013

(65) Prior Publication Data

US 2014/0257288 A1    Sep. 11, 2014

(51) Int. Cl.
*A61B 17/64*  (2006.01)
*A61B 17/66*  (2006.01)

(52) U.S. Cl.
CPC ......... *A61B 17/6466* (2013.01); *A61B 17/6416* (2013.01); *A61B 17/66* (2013.01)

(58) Field of Classification Search
CPC .... A61B 17/60; A61B 17/64; A61B 17/6416; A61B 17/6466; A61B 17/6475; A61B 17/66
USPC ........................ 606/54, 57, 58, 59, 63, 64, 68
See application file for complete search history.

(56) References Cited

U.S. PATENT DOCUMENTS

| | | | |
|---|---|---|---|
| 1,201,864 A | 10/1916 | Overmeyer | |
| 2,251,209 A | 7/1941 | Stader | |
| 2,497,626 A | 2/1950 | Persall | |
| 4,456,004 A | 6/1984 | Kenny | |
| 4,502,473 A | 3/1985 | Harris et al. | |
| 4,548,199 A | 10/1985 | Agee | |
| 4,570,625 A | 2/1986 | Harris et al. | |
| 4,600,000 A | 7/1986 | Edwards | |
| 4,611,586 A | 9/1986 | Agee et al. | |
| 4,628,919 A | 12/1986 | Clyburn | |
| 4,714,076 A * | 12/1987 | Comte et al. | 606/57 |
| 4,730,608 A | 3/1988 | Schlein | |
| 4,895,141 A * | 1/1990 | Koeneman et al. | 606/54 |

(Continued)

FOREIGN PATENT DOCUMENTS

| | | |
|---|---|---|
| EP | 0240034 A1 | 10/1987 |
| EP | 0314021 A2 | 5/1989 |

(Continued)

OTHER PUBLICATIONS

Biomet, DFS Mini Fixator, undated.

(Continued)

*Primary Examiner* — Pedro Philogene
*Assistant Examiner* — David C Comstock
(74) *Attorney, Agent, or Firm* — Lerner, David, Littenberg, Krumholz & Mentlik, LLP

(57) ABSTRACT

Described herein are external fixation systems for correcting bone deformities in adjacent bones or fragments thereof. The systems herein include first and second elongate rods that translate with respect to one another via rotation of an actuation member at an end of one of the rods. At least one housing is coupled along a length of one of the rods. The at least one housing includes at least one pin clamping member for clamping an end of a fixation pin therein. When the at least one pin clamping member is in an unlocked state, the fixation pin can rotate in polyaxial directions. When in a locked state, the angle of fixation wire with respect to the rods is set. The locked and unlocked state of the at least one pin clamping member is determined by the positing of a fixation member with respect to the housing it is coupled to.

19 Claims, 8 Drawing Sheets

(56) References Cited

U.S. PATENT DOCUMENTS

| | | | |
|---|---|---|---|
| 4,968,316 A | 11/1990 | Hergenroeder | |
| 4,988,349 A | 1/1991 | Pennig | |
| 4,998,935 A | 3/1991 | Pennig | |
| 5,122,140 A | 6/1992 | Asche et al. | |
| 5,207,676 A | 5/1993 | Canadell et al. | |
| 5,281,221 A | 1/1994 | Tadych | |
| 5,393,161 A * | 2/1995 | Mata et al. | 403/133 |
| RE34,985 E | 6/1995 | Pennig | |
| 5,429,637 A | 7/1995 | Hardy | |
| 5,437,666 A | 8/1995 | Tepic et al. | |
| 5,545,162 A | 8/1996 | Huebner | |
| 5,601,551 A | 2/1997 | Taylor et al. | |
| 5,620,442 A | 4/1997 | Bailey et al. | |
| 5,624,440 A | 4/1997 | Huebner | |
| 5,658,283 A | 8/1997 | Huebner | |
| 5,662,649 A | 9/1997 | Huebner | |
| 5,674,221 A | 10/1997 | Hein et al. | |
| 5,683,389 A | 11/1997 | Orsak | |
| 5,690,633 A | 11/1997 | Taylor et al. | |
| 5,695,496 A | 12/1997 | Orsak et al. | |
| 5,709,681 A | 1/1998 | Pennig | |
| 5,897,555 A | 4/1999 | Clyburn et al. | |
| 5,976,133 A | 11/1999 | Kraus et al. | |
| 6,010,501 A | 1/2000 | Raskin et al. | |
| 6,080,153 A | 6/2000 | Mata et al. | |
| 6,152,925 A | 11/2000 | Marsh et al. | |
| 6,162,223 A | 12/2000 | Orsak et al. | |
| 6,162,224 A | 12/2000 | Huebner | |
| 6,171,309 B1 | 1/2001 | Huebner | |
| 6,176,860 B1 | 1/2001 | Howard | |
| 6,340,361 B1 | 1/2002 | Kraus et al. | |
| 6,520,961 B1 | 2/2003 | Marsh | |
| 6,575,972 B1 | 6/2003 | Gordon | |
| 6,652,523 B1 | 11/2003 | Evrard et al. | |
| 7,252,669 B1 | 8/2007 | McIntyre | |
| 7,407,504 B2 * | 8/2008 | Dongar et al. | 606/59 |
| 7,608,074 B2 | 10/2009 | Austin et al. | |
| 8,057,473 B2 * | 11/2011 | Orsak et al. | 606/57 |
| 8,206,388 B2 | 6/2012 | Thomke et al. | |
| 8,303,587 B2 | 11/2012 | Lehmann et al. | |
| 2001/0034520 A1 | 10/2001 | Enayati | |
| 2002/0004659 A1 | 1/2002 | Boudard et al. | |
| 2003/0149429 A1 | 8/2003 | Ferrante et al. | |
| 2003/0149430 A1 | 8/2003 | Ferrante et al. | |
| 2004/0097944 A1 | 5/2004 | Koman et al. | |
| 2004/0133199 A1 | 7/2004 | Coati et al. | |
| 2004/0138659 A1 | 7/2004 | Austin et al. | |
| 2005/0113829 A1 | 5/2005 | Walulik et al. | |
| 2006/0229605 A1 | 10/2006 | Olsen | |
| 2006/0235383 A1 | 10/2006 | Hollawell | |
| 2007/0038217 A1 | 2/2007 | Brown et al. | |
| 2007/0100338 A1 | 5/2007 | Deffenbaugh et al. | |
| 2007/0123856 A1 | 5/2007 | Deffenbaugh et al. | |
| 2007/0123857 A1 | 5/2007 | Deffenbaugh et al. | |
| 2007/0233061 A1 | 10/2007 | Lehmann et al. | |
| 2007/0255280 A1 | 11/2007 | Austin et al. | |
| 2008/0221571 A1 | 9/2008 | Daluiski et al. | |
| 2009/0088751 A1 | 4/2009 | Mullaney | |
| 2009/0287212 A1 | 11/2009 | Hirata et al. | |
| 2009/0299368 A1 | 12/2009 | Bauer | |
| 2010/0076436 A1 * | 3/2010 | Hajianpour | 606/59 |
| 2011/0082458 A1 | 4/2011 | Crozet et al. | |
| 2011/0098706 A1 | 4/2011 | Mullaney | |
| 2011/0098707 A1 | 4/2011 | Mullaney | |
| 2011/0172664 A1 | 7/2011 | Bagnasco et al. | |
| 2011/0230882 A1 | 9/2011 | Ben | |
| 2012/0095462 A1 | 4/2012 | Miller | |
| 2012/0150180 A1 | 6/2012 | Verma et al. | |
| 2012/0150184 A1 | 6/2012 | Mullaney | |
| 2012/0150185 A1 | 6/2012 | Mullaney | |
| 2012/0150186 A1 | 6/2012 | Hajianpour | |
| 2012/0203225 A1 | 8/2012 | Mingozzi et al. | |
| 2012/0209266 A1 | 8/2012 | Ottoboni et al. | |
| 2012/0283736 A1 | 11/2012 | Hollawell | |
| 2012/0289959 A1 | 11/2012 | Miller | |
| 2012/0296335 A1 | 11/2012 | Mullaney | |
| 2013/0006244 A1 | 1/2013 | Lehmann et al. | |

FOREIGN PATENT DOCUMENTS

| | | | |
|---|---|---|---|
| EP | 0 469 966 A1 | 2/1992 | |
| EP | 1016381 A1 | 7/2000 | |
| EP | 1254640 A2 | 11/2002 | |
| FR | 2831792 * | 11/2001 | A61B 17/64 |
| GB | 2033758 A | 5/1980 | |
| SU | 1281260 A1 | 1/1987 | |

OTHER PUBLICATIONS

Burny et al., The External Minifixator, Orthopaedic and Trauma Service, University Clinic of Brussels, 1983.

D.N.E., Inc., Pins Anywhere? S.E.A.L. Multi-Plane Mini by D.N.E., undated.

EX FI RE, External Fixation Reduction, Osteo AG, undated.

Mini Rail System, Surgical Technique, SBI, Small Bone Innovations, Inc., 2010.

Original Hoffmann, Mini-Legthening & External Fixation Device, Howmedica, undated.

RX-Fix Surgical Technique, OrthoPro, undated.

The Mini Hoffmann External Fixation System, Howmedica International, undated.

Vilex Rail Fixation System, Vilex, undated.

European Search Report for Application No. EP 14154576 dated Jun. 12, 2014.

* cited by examiner

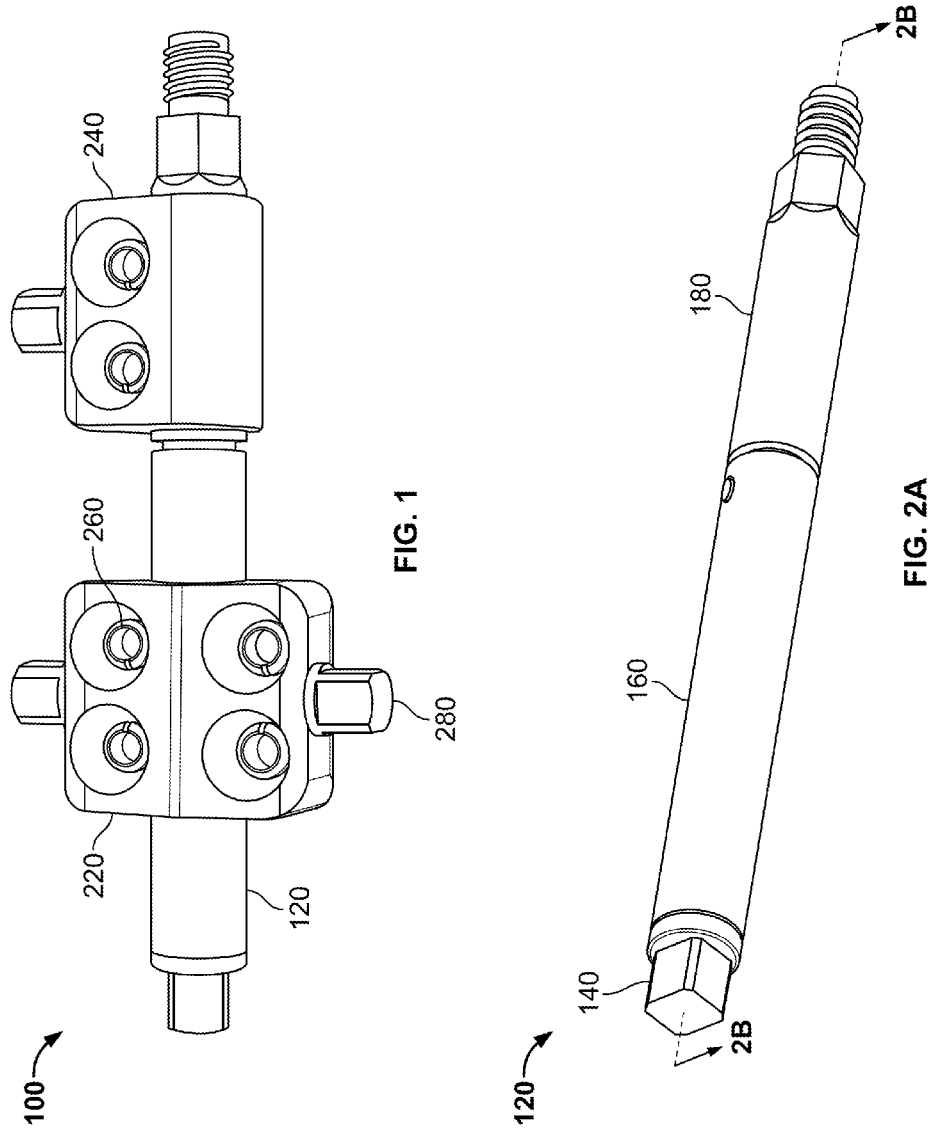

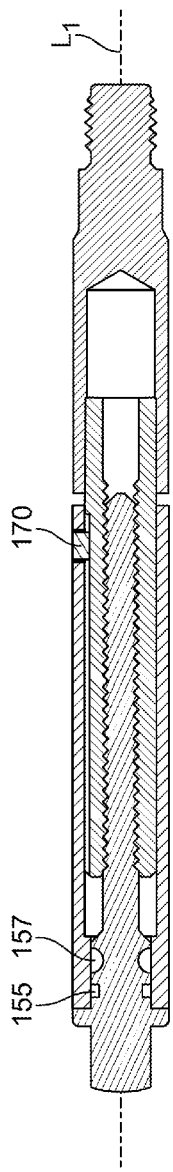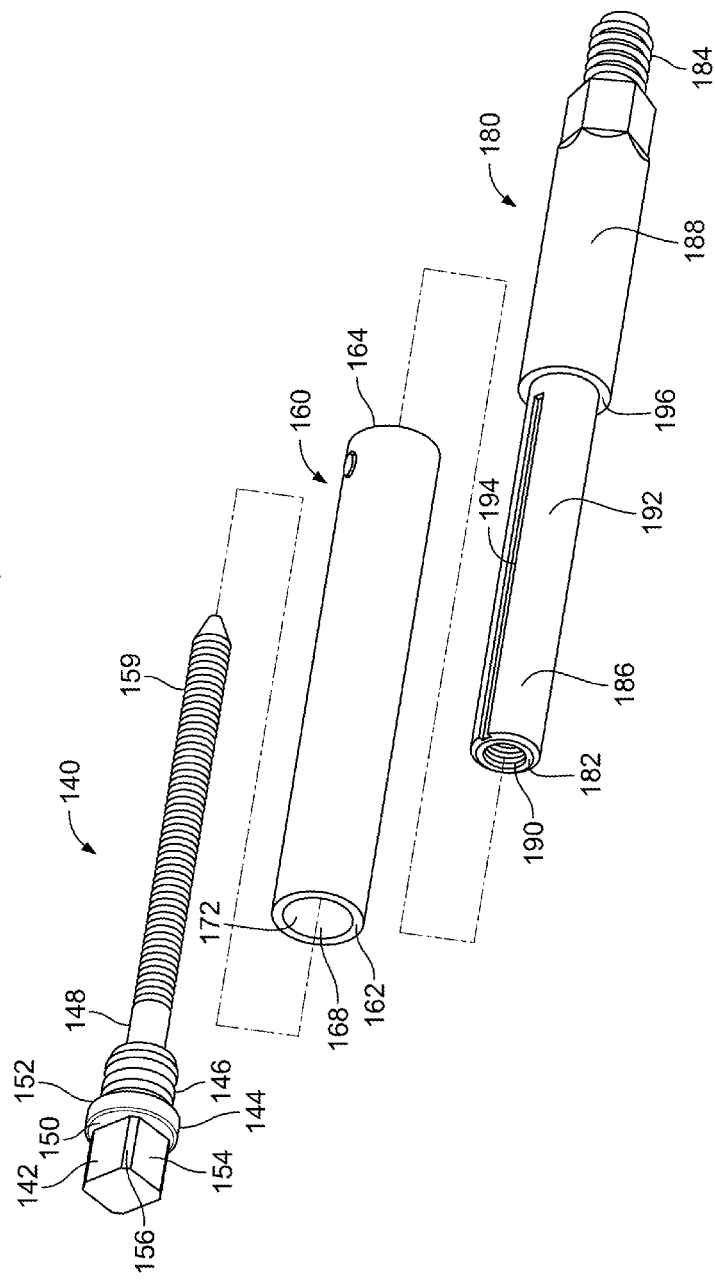

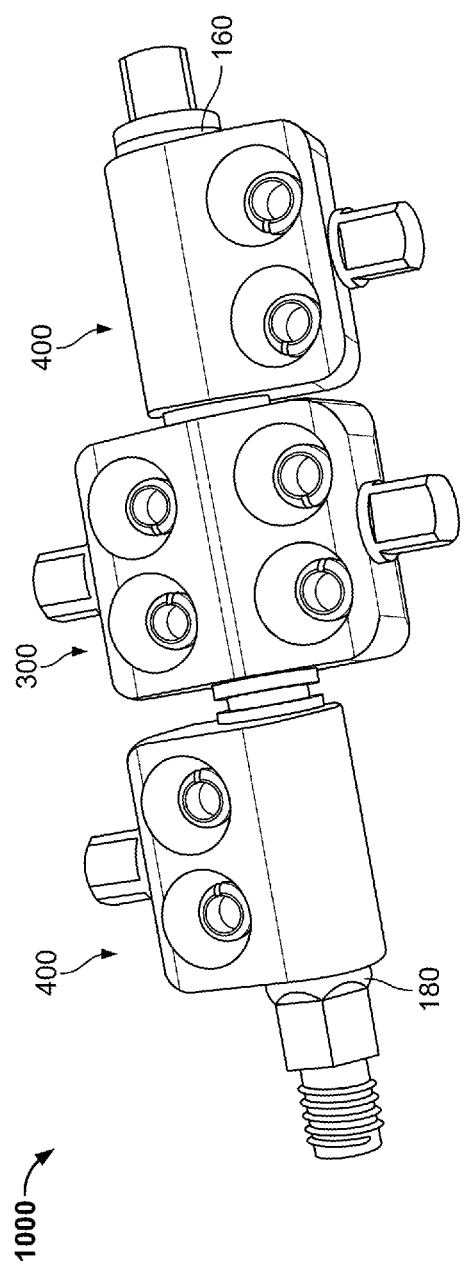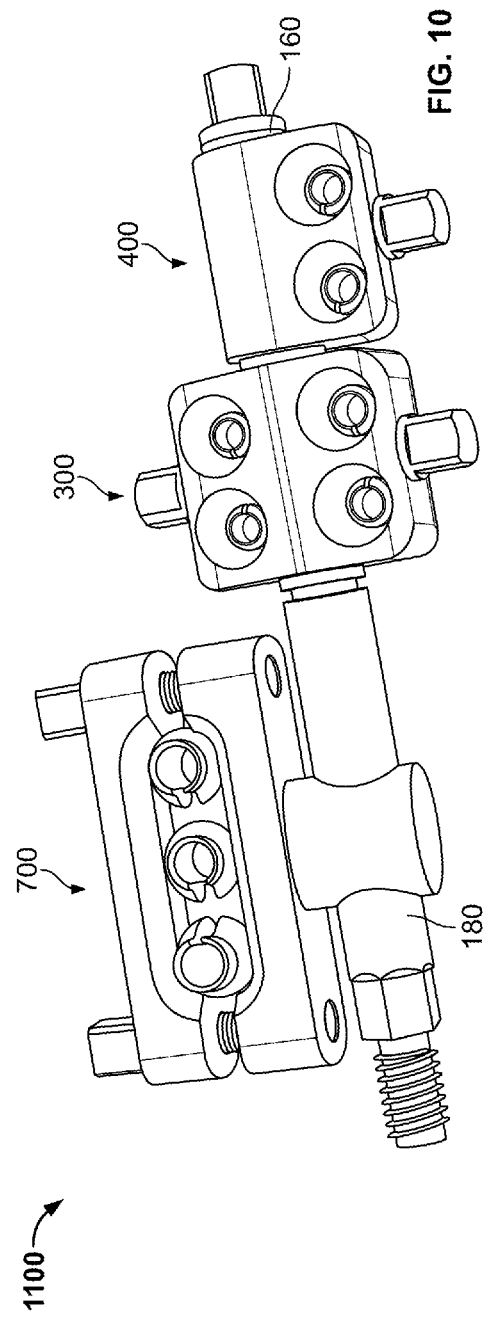

MINI-RAIL EXTERNAL FIXATOR

FIELD OF THE INVENTION

The present invention relates to external fixation systems and methods, and in particular relates to a telescoping body having coupled thereto a ball and socket type pin clamp that allows pin members to have independent trajectories when engaged to both the pin clamp of the external fixation system and a bone of a patient.

BACKGROUND OF THE INVENTION

Many different types of bone deformities can be corrected using external fixation systems. Such systems generally use rings, fixation plates, threaded rods or struts for manipulation, angulation, and translation of the deformities of bones.

Existing fixation systems on the market have many components thereof that are static and do not allow for certain adjustment and/or pivoting. Lack of flexibility in a system may restrict attachment to certain bone areas at certain angles as well as restrict motion of the portion of the body that the external fixation system is being attached to in order to correct. Because of such lack of flexibility, such systems may make it more difficult for the physician to achieve an optimal clinical outcome.

Mini-rails are external fixation systems known in the art that are used to control distraction and compression during lengthening or deformity correction procedures. The primary use of these systems are in the hand, foot and craniomaxillofacial ("CMF") regions. Existing mini-rail systems are generally bulky, unnecessarily complex in procedure, and utilize pin configurations that generally flex during correction of bone fragments.

Further, prior art mini-rails generally consist of exposed threaded rods or "cages" which pin clamps translate on. In other prior art systems, the pin clamps may allow for some polyaxial rotation of the pins that are coupled thereto; however, other degrees of freedom are generally restricted between the pin clamp and the fixation rod that the pin clamp is coupled to. Further, many systems are not configured such that other fixation devices could attach to it unless such other fixation devices are specifically designed to interface with the threaded rod or cage thereof, for example.

There exists a need for a dynamic mini-rail system that is not bulky and allows a pin to be angled with respect to the bone that it is coupled to in almost any translational or rotational degree of freedom such that a physician may target ideal bone for the best pin purchase.

SUMMARY OF THE INVENTION

The present invention improves upon existing mini-rails by allowing for greater flexibility in pin placement. This function allows the physician to target the best bone possible for ideal pin placement and thread purchase. The systems described herein also provide cross platform compatibility by way of a standard 8 mm diameter compression/distraction tube that can easily be coupled to other external fixation devices if desired. Further, the mini-rails of the present invention have a built-in thread such that the mini-rails may be used in other external fixation constructs, such as circular and conventional ex-fix systems, for example.

The mini-rail systems disclosed herein further utilize a ball and socket type pin clamp that allows for independent pin trajectories within a mini-rail construct. The pin clamps are rotatably coupled to a telescoping rod of the mini-rail. This rotation about a longitudinal axis of the telescoping rod may be either in a free or locked state. When the pin clamps are in a locked state, the trajectories of the pins engaged to the pin clamps are preferably fixed.

A first aspect of the present invention is an external fixation device comprising a first elongate rod, a first fixation pin housing, at least one pin clamp member and a locking post member. The first fixation pin housing has at least one vertical bore therethrough and is coupled to the first elongate rod. The at least one pin clamping member is housed at least partially within the at least one vertical bore of the first fixation pin housing and is able to rotate and angulate independently of the first fixation pin housing when in an unlocked state. The first locking post member has a stopper portion and an actuator portion and is coupled to the first fixation pin housing. Movement of the first locking post member in a proximal direction causes compression of the at least one pin clamping member such that the at least one pin clamping member is in a locked state and cannot rotate and angulate independently of the first fixation pin housing.

In accordance with one embodiment of the first aspect of the present invention, the first fixation pin housing preferably has a central longitudinal bore and is coupled to the first elongate rod when at least a portion of the first elongate rod is located within the central longitudinal bore of the first fixation pin housing.

In another embodiment of the first aspect, the first locking post member is preferably coupled to the first fixation pin housing when at least a portion of the stopper portion of the first locking post member is located within a bore of the first fixation pin housing.

In still yet another embodiment of the first aspect, the bore of the first fixation pin housing at least partially cooperates with the central longitudinal bore and the at least one vertical bore of the first fixation pin housing.

In another embodiment of the first aspect, the at least one pin clamping member has a vertical bore adapted to receive at least a portion of a length of a fixation pin there through.

In another embodiment of the first aspect, the at least one pin clamping member is olive shaped with a slit running along a longitudinal length thereof, the at least one pin clamping member having first and second side ends adjacent the slit. The slit preferably has a first width when the at least one pin clamping member is in the unlocked state and a second width less than the first width when the at least one pin clamping member is in the locked state.

In another embodiment of the first aspect, the first fixation pin housing is preferably rotatably coupled to the first elongate rod, and wherein when the at least one pin clamping member is compressed the first fixation pin housing cannot rotate about a longitudinal axis of the first elongate rod.

In another embodiment of the first aspect, a second elongate rod has a longitudinal axis coaxial with a longitudinal axis of the first elongate rod when the first and second elongate rods are coupled, and wherein the first and second elongate rods translate with respect to one another along the longitudinal axes thereof. A second fixation pin housing has at least one vertical bore therethrough and is coupled to the second elongate rod. At least one pin clamping member is housed at least partially within the at least one vertical bore of the second fixation pin housing, the at least one pin clamping member being able to rotate and angulate independently of the second pin housing when in an unlocked state. A second locking post member has a stopper portion and an actuator portion, the second locking post member coupled to the second fixation pin housing, wherein movement of the second locking post member in a proximal direction causes compression of the at least one pin clamping member such that the at least one pin clamping member is in a locked state and cannot rotate and angulate independently of the second fixation pin housing.

In yet another embodiment of the first aspect, an actuation member is rotatably coupled to the first elongate rod such that rotation of the actuation member in a first rotational direction causes the first and second elongate rods to translate along the longitudinal axis thereof away from one another and rotation of the actuation member in a second rotational direction opposite the first rotational direction causes the first and second elongate rods to translate along the longitudinal axis thereof toward one another.

In accordance with a second aspect of the present invention, an external fixation device comprises first and second elongate rods, first and second fixation pin housing, at least one pin clamping member, and first and second locking post members. The first and second elongate rods coupled to one another such that the first and second elongate rods translate with respect to one another along longitudinal axes thereof. The first and second fixation pin housings each have at least one vertical bore therethrough and are coupled to the first and second elongate rods respectively. The at least one pin clamping member housed at least partially within the at least one vertical bore of each of the first and second fixation pin housings is able to rotate and angulate independently of each of the first and second fixation pin housing when in an unlocked state. The first and second locking post members have a stopper portion and an actuator portion and are coupled to each of the first and second fixation pin housings respectively. The at least one pin clamping member housed at least partially within the at least one vertical bore of each of the first and second fixation pin housings is in a locked state when at least a portion of the stopper portion of the first and second locking post members contact the at least one pin clamping member such that the at least one pin clamping member cannot rotate and angulate independently of the first and second fixation pin housings.

BRIEF DESCRIPTION OF THE DRAWINGS

A more complete appreciation of the subject matter of the present invention and the various advantages thereof can be realized by reference to the following detailed description in which reference is made to the accompanying drawings in which:

FIG. 1 is a perspective view of one embodiment of an external fixation system of the present invention.

FIG. 2A is a perspective view of a telescoping rod of the external fixation system of FIG. 1.

FIG. 2B is a cross-section view of the telescoping rod of FIG. 2A taken along line 2B-2B.

FIG. 2C is an exploded perspective view of the telescoping rod of FIG. 2A.

FIG. 9 is a perspective view of yet another embodiment of an external fixation system of the present invention including the first housing shown in FIG. 3A and two of the second housings shown in FIG. 3B with each of the first and second housings coupled to the telescoping rod shown in FIG. 2A.

FIG. 10 is a perspective view of yet another embodiment of an external fixation system of the present invention including the first, second and third housings shown in FIGS. 3, 4A, and 7, respectively, each coupled to the telescoping rod shown in FIG. 2A.

DETAILED DESCRIPTION

Figures 3, 4A, 4B:
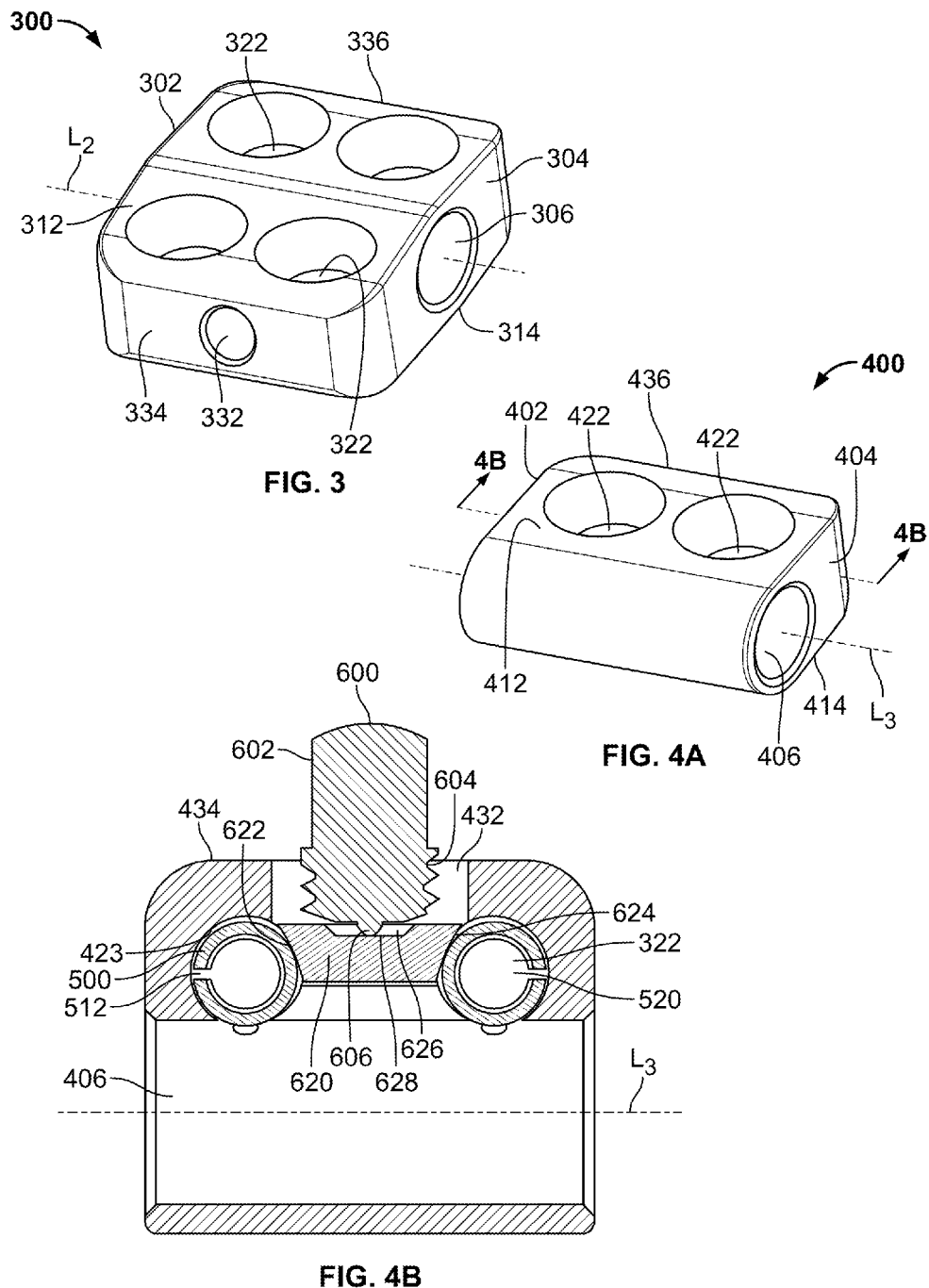
FIG. 3 is a perspective view of a first embodiment of a housing of the external fixation system of FIG. 1.
FIG. 4A is a perspective view of a second embodiment of a housing of the external fixation system of FIG. 1.
FIG. 4B is a cross-section view of the second embodiment of a housing of FIG. 3B taken along line 4B-4B.

Referring to FIGS. 1-6, there is shown an embodiment of an external fixation system 100 having a telescoping rod 120, a first housing 220, a second housing 240, a plurality of pin clamping members 260 and a plurality of locking post members 280.

FIGS. 2A is a perspective view of an assembled telescoping rod 120 having an actuation member 140, a first elongate tube member 160, and a second elongate tube member 180.

As shown in FIGS. 2B and 2C, actuation member 140 includes an actuation portion 142, a base portion 144, an engagement portion 146 and a shaft portion 148. Actuation portion 142 projecting outwardly in a distal direction from a distal end surface 150 of base portion 144. Engagement portion 146 projects outwardly in a proximal direction from a proximal end surface 152 of base portion 144. Shaft portion 148 projects outwardly in a proximal direction from engagement portion 146. Actuation portion 142 is preferably configured to be engaged and manipulated by hand or with a tool. In the embodiment shown, actuation portion 142 has four angled flat surfaces 154 in a square configuration with four rounded edges 156 between adjacent surfaces 154. Engagement portion 146 preferably includes first and second recesses 155, 157. Shaft portion 148 is preferably substantially threaded 159.

First elongate tube member 160 includes a distal end surface 162 and a proximal end surface 164. First elongate tube member has a bore 168 extending through the proximal and distal end surfaces 162, 164 thereof and a protrusion 170 projecting outwardly from an inner surface 172 thereof.

Second elongate tube member 180 includes a distal end surface 182, a proximal end portion 184, a tube portion 186 and a shaft portion 188. Tube portion 186 includes an inner threaded surface 190 and an outer surface 192 having a longitudinal recess 194. Proximal end portion 184 is preferably threaded in order to couple second elongate tube member to other external fixation constructs, if desired.

In assembling telescoping rod 120, distal end surface 162 of first elongate tube member 160 preferably mates with proximal end surface 152 of base portion 144 of actuation member with shaft portion 148 of actuation member 140 being housed within bore 168 of first elongate member. When actuation member 140 is operatively coupled to first elongate tube member 160, engagement portion 146 of actuation member 140 engages inner surface 172 of first elongate tube member 160. Recesses 155, 157 of engagement portion 146 may act as relief portions for coupling purposes or may house a ring member in order to maintain the coupling of actuation member 140 and first elongate tube member 160.

Once actuation member 140 and first elongate tube member 160 are coupled, protrusion 170 of first elongate tube member 160 is coupled to longitudinal recess 194 of tube portion 186 at distal end surface 182 of tube portion 186 and slid along longitudinal recess 194 until threaded portion 159 of shaft portion 148 of actuation member 140 comes in contact with inner threaded surface 190 of tube portion 186 of second elongate tube member 180. Actuation portion 142 is then rotated in a clockwise direction in order to threaded shaft portion 148 onto threaded surface 190. As actuation portion 142 continues to be rotated in a clockwise direction, protrusion 170 continues to ride along longitudinal recess 194 of tube portion 186 in a first direction until proximal end surface 164 lies adjacent a distal end surface 196 of shaft portion 188. Because protrusion 170 rides along longitudinal recess 194, first elongate tube member 160 does not rotate with respect to second elongate tube member 180. Instead, first elongate tube member 160 only translates with respect to second elongate tube 180 along longitudinal axis L1.

If actuation portion 142 is rotated in a counterclockwise direction, protrusion 170 will continue to ride along longitudinal recess 194 of tube portion 186, but in a second direction along longitudinal axis L1 such that proximal end surface 164 will be separated from distal end surface 196 of shaft portion 188 a larger linear distance from one another. As long as actuation member 140, first elongate tube member 160, and second elongate tube member 180 are coupled to one another, rotation of actuation member 140 in either a clockwise or counterclockwise direction will cause proximal end surface 164 and distal end surface 196 to move closer and further away from one another in a linear direction along longitudinal axis L1 of external fixation system 100.

In another embodiment, tube portion 186 of second elongate tube member 180 has an outer surface 192 that is square shaped and has no longitudinal recess 192 in the outer surface thereof. Also, first elongate tube member 160 has a bore 168 having an inner surface 172 that is square shaped and no protrusion 170 projecting outwardly from the inner surface thereof. In this embodiment, once actuation member 140 and first elongate tube member 160 are coupled, square shaped inner surface 172 of first elongate tube member 160 is coupled to square shaped outer surface 192 of tube portion 186 of the second elongate tube member 180 at distal end surface 182 of tube portion 186 and is slid along the outer surface 192 until threaded portion 159 of shaft portion 148 of actuation member 140 comes in contact with inner threaded surface 190 of tube portion 186 of second elongate tube member 180. Actuation portion 142 is then rotated in a clockwise direction in order to threaded shaft portion 148 onto threaded surface 190.

FIG. 3 is a perspective view of a first embodiment of a housing 300 of the external fixation system 100. Housing 300 includes side surfaces 302, 304 having a bore 306 therethrough. Bore 306 defines a longitudinal axis L2 of housing 300. Housing 300 includes a front face 312 and a back face 314 and a plurality of apertures 322 therethrough. Each of the plurality of apertures 322 has a longitudinal axis that is perpendicular and offset to longitudinal axis L2 of housing 300. An internal circumference of each of the plurality of apertures 322 perpendicular to the longitudinal axes of each of the plurality of apertures 322 and is open to bore 306 such that a portion of each of plurality of apertures 322 intersects bore 306. Housing 300 further includes bores 332 extending into housing 300 from bottom and top surfaces 334, 336 thereof. Bores 332 are also open to bore 306 such that a portion of bores 332 intersect bore 306. In the embodiment shown, housing 300 includes four apertures 322. Two of the four apertures are located above longitudinal axis L2 and two of the four apertures are located below longitudinal axis L2.

FIG. 4A is a perspective view of a second embodiment of a housing 400 of the external fixation system 100. Housing 400 includes side surfaces 402, 404 having a bore 406 therethrough. Bore 406 defines a longitudinal axis L3 of housing 400. Housing 400 includes a front face 412 and a back face 414 and a plurality of apertures 422 therethrough. Each of the plurality of apertures 422 has a longitudinal axis that is perpendicular and offset to longitudinal axis L3 of housing 400. An internal circumference of each of the plurality of apertures 422 perpendicular to the longitudinal axes of each of the plurality of apertures 422 and is open to bore 406 such that a portion of each of plurality of apertures 422 intersects bore 406. Housing 400 further includes bore 432 extending into housing 400 from a top surface 436 thereof. Bore 432 is also open to bore 406 such that a portion of bore 432 intersects bore 406. In the embodiment shown, housing 400 includes two apertures 422.

Figure 5:
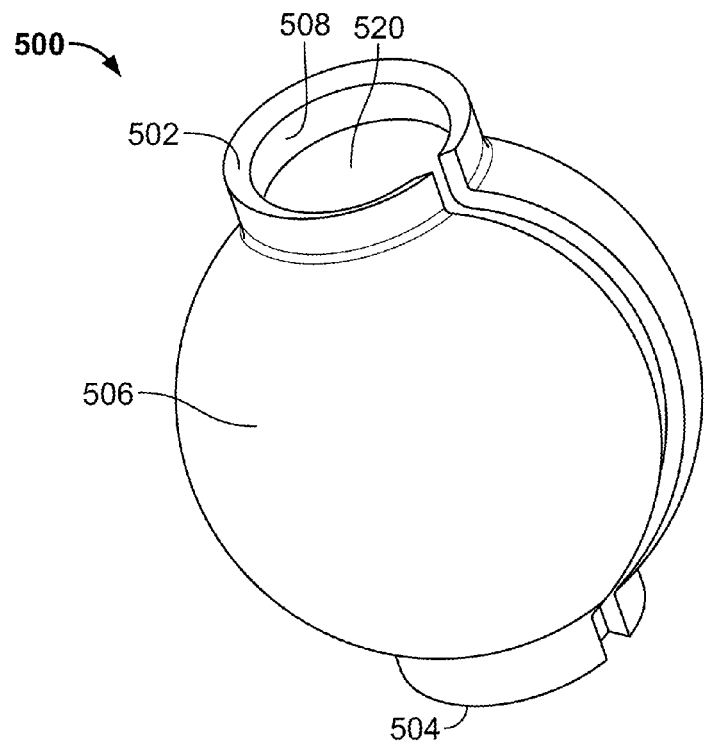
FIG. 5 is a perspective view of a pin clamp of the external fixation system of FIG. 1.
Figure 6:
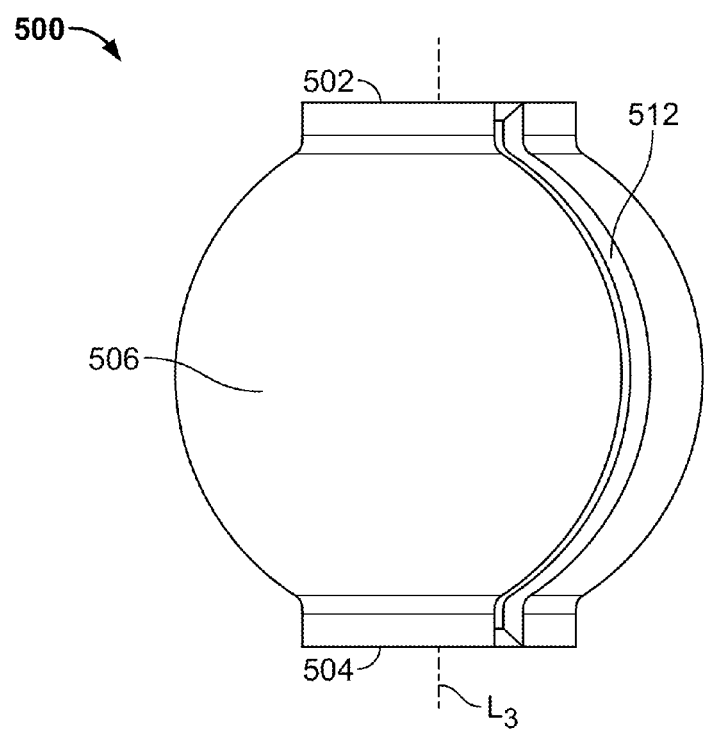
FIG. 6 is a plan view of the pin clamp of FIG. 5.

FIGS. 5-6 are views of one embodiment of a pin clamp 500 that can be used with housings 300, 400 of external fixation system 100. Pin clamp 500 includes side surfaces 502, 504 and an outer circumference surface 506 intermediate side surfaces 502, 504. Side surfaces 502, 504 have an inner surface 508. Pin clamp 500 has a slot 512 that extends through side surface 502, 504 and outer circumference surface 506. Slot 512 provides a resiliency to pin clamp 500 such that if a force is applied to outer circumference surface 506, pin clamp 500 may flex. In flexing, a width of slot 512 is either decreased or increased depending on how the force is applied to outer circumference surface 506. Preferably, slot 512 has a neutral width when pin clamp 500 is in a relaxed state and a lesser width when a force is applied to outer circumference surface 506.

Pin clamp 500 includes a bore 520 extending through side surfaces 502, 504, the bore 520 having a longitudinal axis L3. Bore 520 has a diameter D1 at side surface 502, 504 when pin clamp 500 is in a relaxed state. Upon a force being applied to outer circumference surface 506, bore 520 preferably has a diameter D2 at side surfaces 502, 504. Diameter D2 is preferably less than D1.

FIG. 4B is a cross-section view of housing 400 taken along line 4B-4B of FIG. 4A. In this figure, a clamping mechanism of housing 440 is shown. Clamping mechanism includes an actuation member 600, a wedge member 620, and first and second pin clamps 500 each engaged to housing 400. AS shown in FIG. 4B, pin clamps 500 are housed with apertures 422 of housing 400 and actuation member 600 and wedge member 620 are housed within bore 432 of housing 400.

Actuation member 600 may be referred to as a locking post member having an actuation portion 602, a threaded portion 604 and a protrusion 606. Wedge member 620 includes first and second contact surfaces 622, 624 and a recess portion 626. Protrusion 606 of actuation member 600 is configured to be received in recess portion 626 of wedge member 620 and contact on outer surface 628 of wedge member 620. In other embodiments, actuation member 600 and wedge member 620 are integral such that the clamping mechanism does not include protrusion 606 of actuation member 600 and recess portion 626 and outer surface 628 of wedge member 620.

In another embodiment, protrusion 606 does not projecting outwardly from threaded portion 604. Instead, the base of threaded 604 is rounded. Also, wedge member 620 does not include recess portion 626. In this embodiment, rounded surface of threaded portion 604 interacts with a flat surface of wedge member 620.

In use, pin clamps 500 are received in apertures 422 of housing 400 such that outer circumference surface 506 is located substantially between front and back surfaces 412, 414. Apertures 422 are preferably bounded by inner walls 423 of housing 400. When clamping mechanism of housing 400 is in a neutral state, pin clamps 500 may rotate in polyaxial directions with at least a portion of outer circumference surface 506 contacting inner walls 423. The polyaxial rotation of pin clamps 500 is bounded by the outer circumference surface 506 thereof and the structure surrounding of housing 400.

In order to restrict the polyaxial movement of pin clamps 500 with respect to housing 400, clamping mechanism of housing 400 may be activated. In activating clamping mechanism, actuation member 600 is rotated in a clockwise direction causing the protrusion thereof to move proximally and contact outer surface 628 of wedge member 600. The result of this contact is wedge member 600 also moving in a proximal direction such that first and second contact surfaces 622, 624 thereof contact outer circumference surface 506 of pin clamps 500 and causes the diameter of bore 520 at side surfaces 502, 504 of pin clamps 500 to decrease. Pin clamps 500 also move in a proximal fashion when actuation member 600 is rotated in a clockwise direction. In order to bring clamping mechanism back to a neutral state, actuation member 500 is rotated in a counterclockwise direction.

As shown in FIG. 1, housing 400 is coupled to shaft portion 188 of second elongate tube member 180. When clamping mechanism is in a neutral state, housing 400 may rotate with respect to second elongate tube member 180 such that longitudinal axis L3 of housing 400 may rotate with respect to longitudinal axis L1 of external fixation system 100 even though longitudinal axis L1 and L3 are preferably coaxial. When clamping mechanism is activated, wedge member 620 compresses pin clamps 500 between contact surfaces 622, 624 thereof and shaft portion 188 of second elongate tube member 180. Another result of activation of the clamping mechanism is that housing 400 preferably can no longer rotate with respect to second elongate tube member 180.

The same clamping mechanism of housing 400 that is shown in FIG. 4B is also included in housing 300 except that housing 300 preferably includes two separate clamping mechanisms on each side of longitudinal axis L2 thereof. As shown in FIG. 1, housing 300 is coupled to an outer surface of first elongate tube member 160. When the clamping mechanisms thereof are in a neutral state, housing 300 may rotate with respect to first elongate tube member 160 such that longitudinal axis L2 of housing 300 may rotate with respect to longitudinal axis L1 of external fixation system 100 even though longitudinal axis L1 and L2 are preferably coaxial. When either clamping mechanism of housing 300 is activated, a wedge member thereof preferably compresses pin clamps 500 between contact surfaces of the wedge member and outer surface of first elongate tube member 160. Another result of activation of either clamping mechanism 300 is that housing 300 preferably can no longer rotate with respect to first elongate tube member 160.

The present invention provides a dynamic mini-rail that allows for many degrees of freedom between components parts thereof. First and second elongate tube members 160, 180 may translate with respect to one another. Housings 300 and 400 may rotate with respect to first and second elongate tube members 160, 180 and housings 300 and 400 may rotate about first and second elongate tube members 160, 180 with respect to one another. Pin clamps 500 may rotate at independent trajectories while housed within housings 300.

Figure 7:
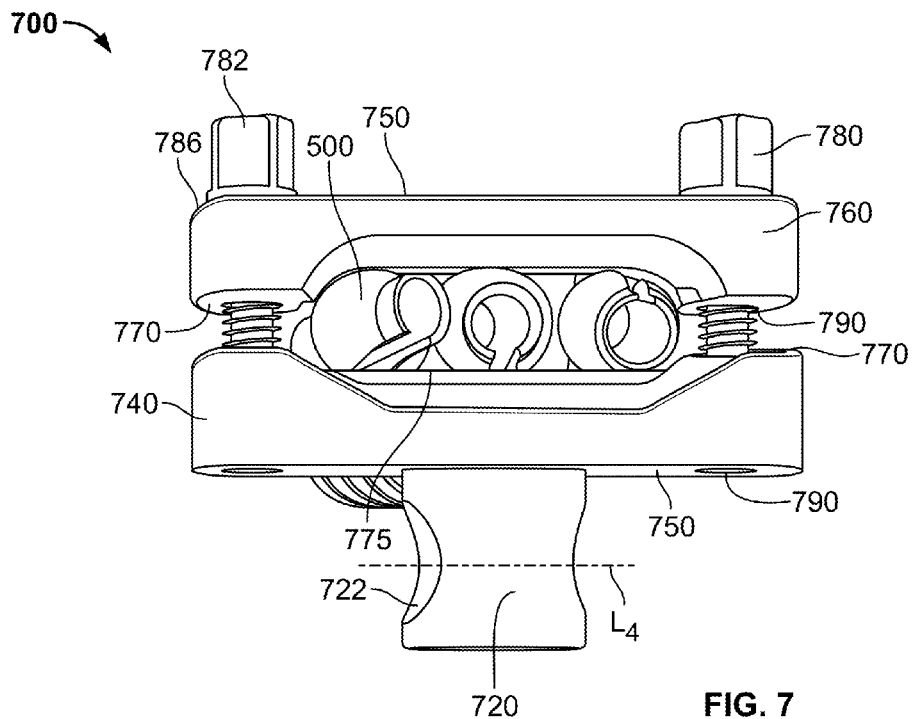
FIG. 7 is a perspective view of a third embodiment of a housing of the present invention that can be coupled to a telescoping rod such as shown in FIG. 2A.

FIG. 7 is a perspective view of a third embodiment of a housing 700 of the present invention. Housing 700 includes a base member 720, first and second plate members 740, 760, a plurality of pin clamps 500, and first and second fixation post members 780. Base member 720 is coupled to a clamping mechanism that includes bottom and top plate members 740, 760, the plurality of pin clamps 500 and first and second fixation post members 780. Base member 720 has a bore 722 therethrough and a longitudinal axis L4. A longitudinal axis of first and second plate members 740, 760 is preferably parallel with longitudinal axis L4 of base member 720, but may be angled with respect to longitudinal axis L4 of base member 720.

First and second plate members 740, 760 each have a threaded vertical bore 790 extending through outwardly and inwardly facing surfaces 750, 770 thereof. First and second plate members 740, 760 further have a longitudinal recess 775 in the inwardly facing surfaces 770 thereof. Longitudinal recess 775 is shaped to receive a portion of outer circumference surface 506 of the plurality of pin clamps 500 in order to couple and partially house the plurality of pin clamps 500 with respect to first and second plate members 740, 760.

Fixation post members 780 have a head portion 782 and a threaded shaft portion 784. Threaded shaft portion 784 of fixation post members is received and threaded into vertical bore 790 of first and second plate member 740, 760. Upon threading of fixation post members into vertical bores 790 of first and second plate members 740, 760, a bottom surface 786 of head portion 782 of fixation post members 780 presses against outwardly facing surface 750 of one of the first and second plate members 740, 760 and cases the inwardly facing surfaces 770 of the first and second plate members 740, 760 to move closer to one another such that the plurality of pin clamps 500 become compressed.

Figure 8:
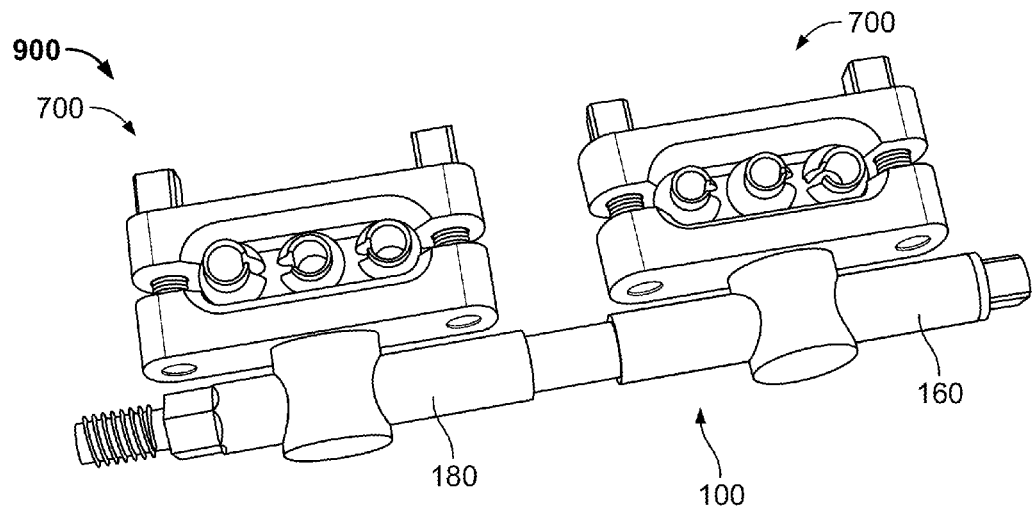
FIG. 8 is a perspective view of another embodiment of an external fixation system of the present invention including two of the third housings shown in FIG. 7 each coupled to the telescoping rod shown in FIG. 2A.

FIG. 8 is a perspective view of another embodiment of an external fixation system 900 of the present invention including two of the third housings 700 shown in FIG. 7 each coupled to the telescoping rod 100 shown in FIG. 2A. One of the third housings 700 is coupled to a first elongate tube member 160 and the other of the third housings 700 is coupled to a second elongate tube member 180.

FIG. 9 is a perspective view of yet another embodiment of an external fixation system 1000 of the present invention including first housing 300 coupled to second elongate tube member 180 and first housing 300 and second housing 400 coupled to first elongate tube member 160.

FIG. 10 is a perspective view of yet another embodiment of an external fixation system 1100 of the present invention including third housing 700 coupled to second elongate tube member 180 and first housing 300 and second housing 400 coupled to first elongate tube member 160.

Figure 11:
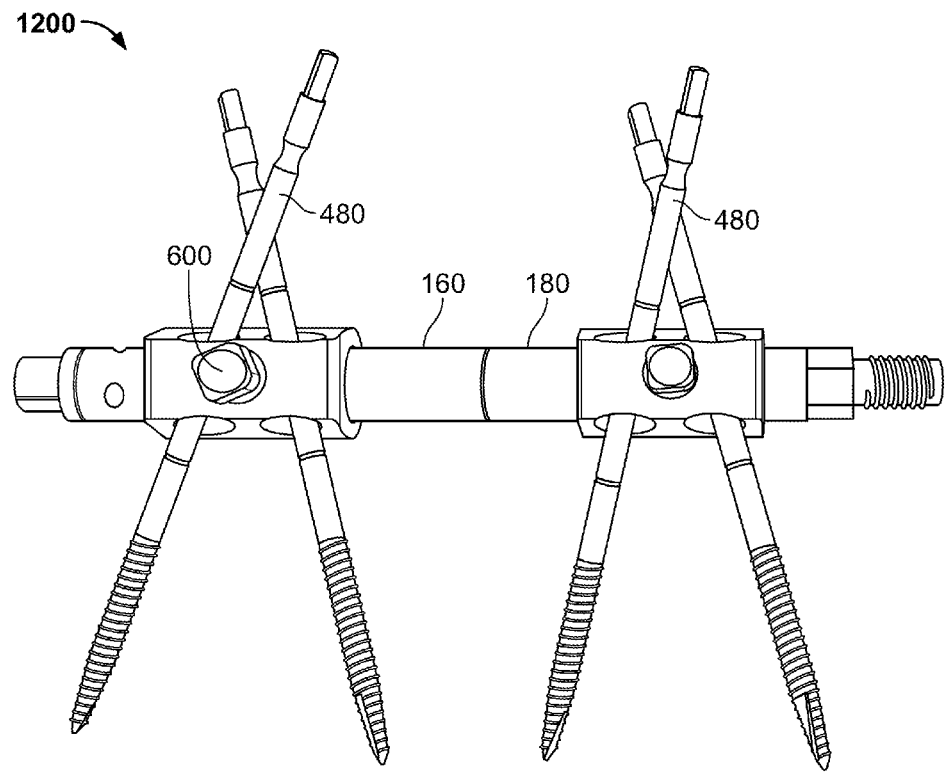
FIG. 11 is a perspective view of yet another embodiment of an external fixation system having a plurality of pins engaged to housings with the pins having independent pin trajectories.

FIG. 11 is a perspective view of yet another embodiment of an external fixation system 1200 of the present invention including second housing 400 coupled to second elongate tube member 180 and second housing 400 coupled to first elongate tube member 160. A plurality of pins 480 are received and housed with pin clamps 500 of housings 400. The plurality of pins 480 have independent pin trajectories with respect to one another. In activating clamping mechanism of housings 400, actuation member 600 is rotated in a clockwise direction causing it to move proximally and compress outer circumference surface 506 of pin clamps 500 and causes the diameter of bore 520 at side surfaces 502, 504 of pin clamps 500 to decrease. The result of activating the clamping mechanism of housings 400 is the pin clamps 500 cannot rotate and angulate independently of housing 400. In order to bring clamping mechanism back to a neutral state, actuation member 500 is rotated in a counterclockwise direction, which will also pin clamps 500 housing pins 480 to rotate and angulate with respect to housings 400 once again.

Figure 12:
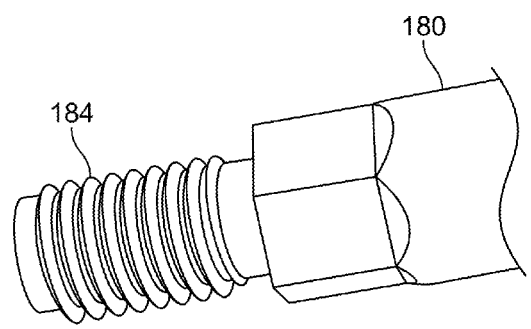
FIG. 12 is a partial view showing an end of telescoping rod shown in FIG. 2A having a built-in thread such that the telescoping rod may be coupled to other external fixation constructs.
Figure 13A:
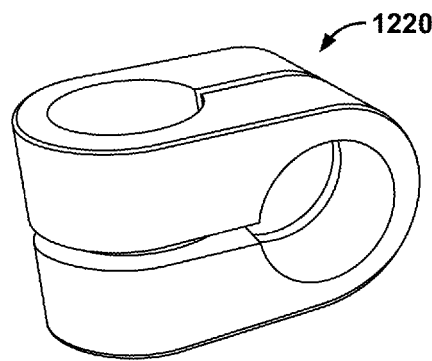
FIG. 13A is an embodiment of a bolt adapter that can be coupled to a telescoping rod of the present invention.
Figure 13B:
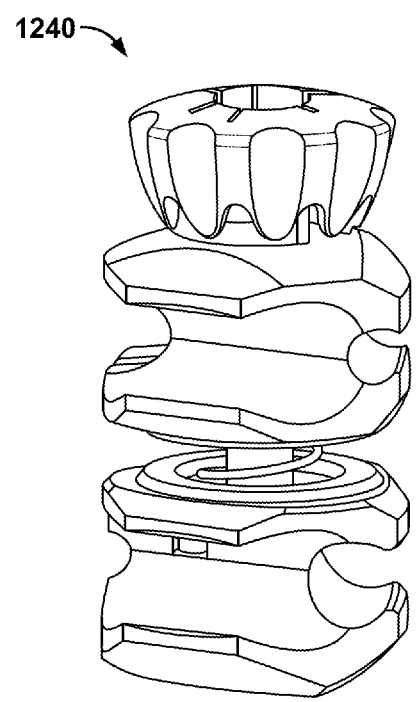
FIG. 13B is an embodiment of a rod clamp that can be coupled to a telescoping rod of the present invention.
Figure 13C:
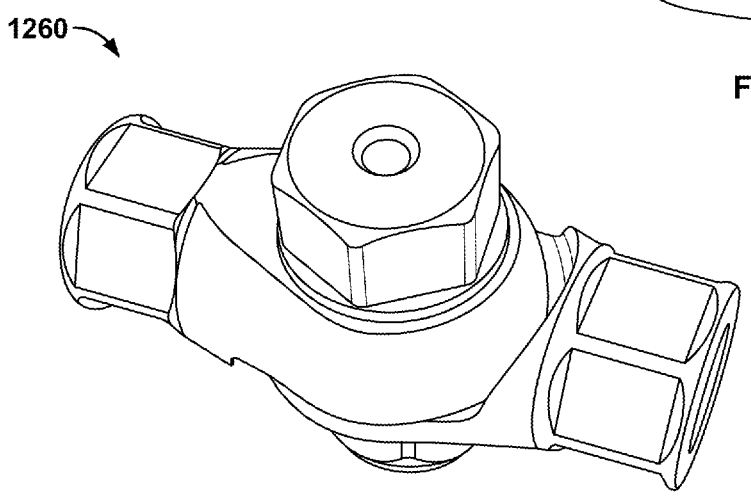
FIG. 13C is an embodiment of a hinge coupling that can be coupled to a telescoping rod of the present invention.

FIG. 12 is a partial view showing an end of second elongate tube member 180 of a telescoping rod having a built-in thread 184 such that the telescoping rod may be coupled to other external fixation constructs. Such constructs, for example, are shown in FIGS. 13A-13C, which are a bolt adapter 1220, a rod clamp 1240, and a hinge coupling 1260, respectively. These coupling mechanism are all known in the art of external fixation systems and all the external fixation systems of the present invention to be compatible with such constructs.

In a method of correcting a bone deformity of the present invention, an external fixation system having a plurality of housings (may be housing 300, 400 or 700) are coupled to a telescoping rod 100. A plurality of pins such as those shown in FIG. 11 are coupled to the housings. One end of the pins are received in pin clamps housed within the housings and another end of the pins are engaged to bone at or adjacent to the deformity in the bone being corrected. A first end of pins are preferably engaged to bone. A second end of pins are then received through a bore hole in a pin clamp coupled to a housing, the housing coupled to a telescoping rod. Additional pins engaged at one end to bone may all be received through a bore hole in another pin clamp coupled to the housing or a different housing coupled to a telescoping rod. Once the desired number of pins are engaged to bone and the other ends of the pins are coupled to pin clamps, the fixation or set screws of the housing may then be tightened to set the angle of the pins with respect to the housings each are coupled to.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An external fixation system comprising:
   a first elongate rod;
   a first fixation pin housing having a longitudinal bore housing at least a portion of the first elongate rod;
   at least one pin clamping member housed at least partially within the first fixation pin housing, the at least one pin clamping member being moveable with respect to the first fixation pin housing and the first elongate rod when in an unlocked state; and
   a first locking post member coupled to the first fixation pin housing,
   wherein movement of the first locking post member in a proximal direction causes the at least one pin clamping member to directly contact and compress against the first elongate rod such that the at least one pin clamping member is in a locked state and cannot move with respect to the first fixation pin housing and first elongate rod.

2. The external fixation system of claim 1, further including an actuator portion and a stopper portion of the first locking post member, the first locking port member being coupled to the first fixation pin housing when at least a portion of the stopper portion of the first locking post member is located within a bore of the first fixation pin housing.

3. The external fixation system of claim 2, wherein the bore of the first fixation pin housing at least partially cooperates with the longitudinal bore and an at least one vertical bore of the first fixation pin housing, the at least one pin clamping member housed at least partially within the at least one vertical bore of the first fixation pin housing.

4. The external fixation system of claim 1, wherein the at least one pin clamping member has a vertical bore adapted to receive at least a portion of a length of a fixation pin therethrough.

5. The external fixation system of claim 1, wherein the at least one pin clamping member is olive shaped with a slit running along a longitudinal length thereof, the at least one pin clamping member having first and second side ends adjacent the slit.

6. The external fixation system of claim 5, wherein the slit has a first width when the at least one pin clamping member is in the unlocked state and a second width less than the first width when the at least one pin clamping member is in the locked state.

7. The external fixation system of claim 1, wherein the first fixation pin housing is rotatably coupled to the first elongate rod, and wherein when the at least one pin clamping member is compressed against the first elongate rod, the first fixation pin housing cannot rotate about a longitudinal axis of the first elongate rod.

8. The external fixation system of claim 1, further comprising a second elongate rod having a longitudinal axis coaxial with a longitudinal axis of the first elongate rod when the first and second elongate rods are coupled, and wherein the first and second elongate rods translate with respect to one another along the longitudinal axes thereof.

9. The external fixation system of claim 8, further comprising:
   a second fixation pin housing coupled to the second elongate rod; and
   at least one pin clamping member housed at least partially within the second fixation pin housing, the at least one pin clamping member being moveable with respect to the second fixation pin housing when in an unlocked state; and
   a second locking post member coupled to the second fixation pin housing,
   wherein movement of the second locking post member in a proximal direction causes the at least one pin clamping member to compress against the second elongate rod such that the at least one pin clamping member is in a locked state and cannot move with respect to the second fixation pin housing and second elongate rod.

10. The external fixation system of claim 9, wherein an actuation member is rotatably coupled to the first elongate rod such that rotation of the actuation member in a first rotational direction causes the first and second elongate rods to translate along the longitudinal axes thereof away from one another and rotation of the actuation member in a second rotational direction opposite the first rotational direction causes the first and second elongate rods to translate along the longitudinal axes thereof toward one another.

11. An external fixation system comprising:
first and second elongate rods coupled to one another such that the first and second elongate rods translate with respect to one another along longitudinal axes thereof;
first and second fixation pin housings coupled to the first and second elongate rods respectively; and
at least one pin clamping member housed at least partially within each of the first and second fixation pin housings,
wherein each of the at least one pin clamping members are moveable between an unlocked state at which each of the at least one pin clamping members are able to move independently with respect to the first or second fixation pin housing it is at least partially housed within and the at least first and second elongate rods respectively and a locked state at which each of the at least one pin clamping members are fixed with respect to the first or second fixation pin housing it is at least partially housed within and directly contacts and is compressed against the first and second elongate rods respectively.

12. The external fixation system of claim 11, further including a longitudinal bore in each of the first and second pin housings in which the first and second elongate rods may respectively be located.

13. The external fixation system of claim 12, further including first and second locking post members coupled to the first and second fixation pin housings respectively, when at least a portion of a stopper portion the first and second locking post members are located within a bore of the first and second fixation pin housings respectively.

14. The external fixation system of claim 13, wherein the bore of each of the first and second fixation pin housings at least partially cooperates with the longitudinal bore and the at least one vertical bore of each of the first and second fixation pin housings respectively.

15. The external fixation system of claim 11, wherein the at least one pin clamping member has a vertical bore adapted to receive at least a portion of a length of a fixation pin therethrough.

16. The external fixation system of claim 11, wherein the at least one pin clamping member is olive shaped with a slit running along a longitudinal length thereof, the at least one pin clamping member having first and second side ends adjacent the slit.

17. The external fixation system of claim 16, wherein the slit has a first width when the at least one pin clamping member is in the unlocked state and a second width less than the first width when the at least one pin clamping member is in the locked state.

18. The external fixation system of claim 11, wherein the first fixation pin housing is rotatably coupled to the first elongate rod, and wherein when the at least one pin clamping member thereof is compressed against the first elongate rod, the first fixation pin housing cannot rotate about the longitudinal axis of the first elongate rod.

19. The external fixation system of claim 18, wherein the second fixation pin housing is rotatably coupled to the second elongate rod, and wherein when the at least one pin clamping member thereof is compressed against the second elongate rod, the second fixation pin housing cannot rotate about the longitudinal axis of the second elongate rod.

* * * * *